(12) United States Patent
Callahan et al.

(10) Patent No.: US 9,375,162 B2
(45) Date of Patent: Jun. 28, 2016

(54) ECG LEADWIRE SYSTEM WITH NOISE SUPPRESSION AND RELATED METHODS

(71) Applicant: Covidien LP, Mansfield, MA (US)

(72) Inventors: Mark J. Callahan, Medway, MA (US);
Glenn Gilbert, Plymouth, MA (US);
Scott R. Coggins, Littleton, MA (US);
Linda D'Elia, Westfield, MA (US)

(73) Assignee: Covidien LP, Mansfield, MA (US)

( * ) Notice: Subject to any disclaimer, the term of this patent is extended or adjusted under 35 U.S.C. 154(b) by 3 days.

(21) Appl. No.: 14/135,239

(22) Filed: Dec. 19, 2013

(65) Prior Publication Data
US 2014/0221856 A1    Aug. 7, 2014

Related U.S. Application Data

(62) Division of application No. 13/249,450, filed on Sep. 30, 2011, now Pat. No. 8,634,901.

(51) Int. Cl.
*A61B 5/0428*    (2006.01)
*A61B 5/0402*    (2006.01)
(Continued)

(52) U.S. Cl.
CPC ........... *A61B 5/04286* (2013.01); *A61B 5/0402* (2013.01); *A61B 5/04017* (2013.01); *A61B 5/7217* (2013.01); *H01F 17/06* (2013.01);
(Continued)

(58) Field of Classification Search
CPC ............. A61B 5/0402; A61B 5/04017; A61B 5/7203; A61B 5/7217; A61B 2562/222; A61N 1/3718; A61N 2001/086; A61N 1/16; A61N 1/375; A61N 1/3925; A61N 1/08; H01R 2201/12; A61F 2210/009; Y10T 428/24992; Y10T 428/25; Y10T 428/27; Y10T 428/2982

USPC ............... 607/1–2, 9, 27, 36–38, 115; 600/508–509
See application file for complete search history.

(56) References Cited

U.S. PATENT DOCUMENTS 4,832,608 A    5/1989    Kroll
4,885,559 A    12/1989    Nakano
(Continued)

FOREIGN PATENT DOCUMENTS

EP    2 314 215    4/2011

OTHER PUBLICATIONS

European Office Action dated May 9, 2014; for European Pat. App. No. 12778168.0; 2 pages.
(Continued)

*Primary Examiner* — Deborah Malamud

(57) ABSTRACT

A noise-suppressing electrocardiograph (ECG) adapter having a first end, a second end, and a noise-suppression element is presented, together with an ECG noise-suppressing system and related methods. In an embodiment, the noise-suppressing ECG adapter includes a housing having at least one first connector disposed at a first end of the housing adapted to electrically couple with an ECG lead set, and at least one second connector adapted for coupling to an input of an ECG device. The adapter includes a noise suppression element. The noise suppression element includes a ferromagnetic element having an opening defined therein. In an embodiment the noise suppression element is internal to the adapter. In another embodiment, the noise suppression element is tethered externally to the adapter and configured to clamp around at least a portion of an ECG leadwire.

16 Claims, 7 Drawing Sheets

(51) Int. Cl.
*H01R 13/719* (2011.01)
*H01R 31/06* (2006.01)
*H05K 9/00* (2006.01)
*H01F 17/06* (2006.01)
*A61B 5/04* (2006.01)
*A61B 5/00* (2006.01)
*H03H 1/00* (2006.01)

(52) U.S. Cl.
CPC ............ *H01R13/719* (2013.01); *H01R 31/065* (2013.01); *H05K 9/0066* (2013.01); *A61B 2562/182* (2013.01); *A61B 2562/227* (2013.01); *H01F 2017/065* (2013.01); *H01R 2201/12* (2013.01); *H03H 2001/005* (2013.01)

(56) References Cited

U.S. PATENT DOCUMENTS

| | | |
|---|---|---|
| 5,080,604 A | 1/1992 | Rider et al. |
| 5,083,238 A | 1/1992 | Bousman |
| 5,083,933 A | 1/1992 | Colleran et al. |
| 5,091,707 A | 2/1992 | Wollmerschauser et al. |
| 5,104,253 A | 4/1992 | Zielinski et al. |
| 5,104,334 A | 4/1992 | Honma et al. |
| 5,131,854 A | 7/1992 | Jose et al. |
| 5,137,466 A | 8/1992 | Endo et al. |
| 5,154,646 A | 10/1992 | Shoup |
| 5,158,469 A | 10/1992 | Martin |
| 5,160,276 A | 11/1992 | Marsh et al. |
| 5,173,059 A | 12/1992 | Sato et al. |
| 5,176,343 A | 1/1993 | Cheney, II et al. |
| 5,178,556 A | 1/1993 | Chen |
| 5,180,312 A | 1/1993 | Martin |
| 5,190,467 A | 3/1993 | Ohta |
| 5,192,226 A | 3/1993 | Wang |
| 5,197,901 A | 3/1993 | Hashiguchi |
| 5,199,897 A | 4/1993 | Hashiguchi |
| 5,201,669 A | 4/1993 | Lin |
| 5,203,715 A | 4/1993 | Yamamoto |
| 5,203,719 A | 4/1993 | Kozono |
| 5,232,383 A | 8/1993 | Barnick |
| 5,234,356 A | 8/1993 | Macjima et al. |
| 5,234,357 A | 8/1993 | Yamaguchi |
| 5,243,510 A | 9/1993 | Chaney, II |
| 5,276,443 A | 1/1994 | Gates et al. |
| 5,278,759 A | 1/1994 | Berra et al. |
| 5,293,013 A | 3/1994 | Takahashi |
| 5,320,621 A | 6/1994 | Gordon et al. |
| 5,326,272 A | 7/1994 | Harhen et al. |
| 5,331,549 A | 7/1994 | Crawford, Jr. |
| 5,332,330 A | 7/1994 | Kaneko |
| 5,334,955 A | 8/1994 | Strnad |
| 5,338,219 A | 8/1994 | Hiramoto et al. |
| 5,341,806 A | 8/1994 | Gadsby et al. |
| 5,341,812 A | 8/1994 | Allaire et al. |
| 5,362,249 A | 11/1994 | Carter |
| 5,370,116 A | 12/1994 | Rollman et al. |
| 5,370,550 A | 12/1994 | Alwine et al. |
| 5,376,016 A | 12/1994 | Inaba et al. |
| 5,378,168 A | 1/1995 | Sumida |
| 5,380,223 A | 1/1995 | Marsh et al. |
| 5,382,176 A | 1/1995 | Norden |
| 5,383,794 A | 1/1995 | Davis et al. |
| 5,387,116 A | 2/1995 | Wang |
| 5,387,127 A | 2/1995 | Wang |
| 5,399,045 A | 3/1995 | Yoneda et al. |
| 5,415,164 A | 5/1995 | Faupel et al. |
| 5,429,526 A | 7/1995 | Ann |
| 5,454,739 A | 10/1995 | Strand |
| 5,462,448 A | 10/1995 | Kida et al. |
| 5,486,117 A | 1/1996 | Chang |
| 5,507,665 A | 4/1996 | Oda |
| 5,507,668 A | 4/1996 | Lambrinos et al. |
| 5,509,822 A | 4/1996 | Negus et al. |
| 5,511,546 A | 4/1996 | Hon |
| 5,546,950 A | 8/1996 | Schoeckert et al. |
| 5,558,526 A | 9/1996 | Nagamine |
| 5,558,534 A | 9/1996 | Sarkady et al. |
| 5,558,535 A | 9/1996 | Saka et al. |
| 5,564,939 A | 10/1996 | Maitani et al. |
| 5,584,719 A | 12/1996 | Tsuji et al. |
| 5,599,199 A | 2/1997 | Wright |
| 5,603,632 A | 2/1997 | Johannes et al. |
| 5,611,708 A | 3/1997 | Mizunuma et al. |
| 5,613,870 A | 3/1997 | Traver, Jr. |
| 5,615,674 A | 4/1997 | Maurer |
| 5,622,168 A | 4/1997 | Keusch et al. |
| 5,624,271 A | 4/1997 | Childs et al. |
| 5,626,135 A | 5/1997 | Sanfilippo |
| 5,632,274 A | 5/1997 | Quedens et al. |
| 5,632,643 A | 5/1997 | Shepherd et al. |
| 5,651,689 A | 7/1997 | Plyler et al. |
| 5,653,606 A | 8/1997 | Chrysostomou |
| 5,674,088 A | 10/1997 | Roche et al. |
| 5,676,694 A | 10/1997 | Boser et al. |
| 5,679,022 A | 10/1997 | Cappa et al. |
| 5,679,029 A | 10/1997 | Saunier et al. |
| 5,695,355 A | 12/1997 | Hasenfratz et al. |
| 5,702,265 A | 12/1997 | Yamaguchi |
| 5,711,684 A | 1/1998 | Inoue et al. |
| 5,718,596 A | 2/1998 | Inaba et al. |
| 5,724,984 A | 3/1998 | Arnold et al. |
| 5,725,525 A | 3/1998 | Kordis |
| 5,741,155 A | 4/1998 | Herman |
| 5,749,746 A | 5/1998 | Tan et al. |
| 5,769,650 A | 6/1998 | Aoyama et al. |
| 5,772,591 A | 6/1998 | Cram |
| 5,775,953 A | 7/1998 | Yamanashi et al. |
| 5,782,647 A | 7/1998 | Okura et al. |
| 5,782,892 A | 7/1998 | Castle et al. |
| 5,788,527 A | 8/1998 | Sanders et al. |
| 5,797,854 A | 8/1998 | Hedgecock |
| 5,806,152 A | 9/1998 | Saitou et al. |
| 5,813,404 A | 9/1998 | Devlin et al. |
| 5,813,979 A | 9/1998 | Wolfer |
| 5,827,086 A | 10/1998 | Fukuda |
| 5,830,000 A | 11/1998 | Shifflett et al. |
| 5,836,783 A | 11/1998 | Morisawa et al. |
| 5,843,141 A | 12/1998 | Bischoff et al. |
| 5,848,456 A | 12/1998 | Sjoqvist |
| 5,873,747 A | 2/1999 | Tsuji |
| 5,876,232 A | 3/1999 | Matsushita et al. |
| 5,895,284 A | 4/1999 | Kocher et al. |
| 5,904,579 A | 5/1999 | McLean et al. |
| 5,931,689 A | 8/1999 | Patel |
| 5,931,861 A | 8/1999 | Werner et al. |
| 5,934,926 A | 8/1999 | Gabrisko, Jr. et al. |
| 5,937,950 A | 8/1999 | Adams et al. |
| 5,938,470 A | 8/1999 | Kashiyama |
| 5,941,725 A | 8/1999 | Brennan et al. |
| 5,951,316 A | 9/1999 | Kawano et al. |
| 5,964,624 A | 10/1999 | Pernelle |
| 5,968,087 A | 10/1999 | Hess et al. |
| 5,971,790 A | 10/1999 | Rohde |
| 5,971,799 A | 10/1999 | Swade |
| 5,980,332 A | 11/1999 | Tsuji et al. |
| 5,984,717 A | 11/1999 | Lee |
| 5,997,334 A | 12/1999 | Goto |
| 6,027,359 A | 2/2000 | Aoki et al. |
| 6,032,063 A | 2/2000 | Hoar et al. |
| 6,032,064 A | 2/2000 | Devlin et al. |
| 6,038,479 A | 3/2000 | Werner et al. |
| 6,038,481 A | 3/2000 | Werner et al. |
| 6,050,838 A | 4/2000 | Norizuki et al. |
| 6,062,892 A | 5/2000 | Meng et al. |
| 6,062,902 A | 5/2000 | Buckles et al. |
| 6,074,234 A | 6/2000 | Hasegawa |
| 6,098,127 A | 8/2000 | Kwang |
| 6,109,948 A | 8/2000 | Kuo |
| 6,115,623 A | 9/2000 | McFee |
| 6,116,940 A | 9/2000 | Bertens |
| 6,116,941 A | 9/2000 | Kuo |
| 6,129,666 A | 10/2000 | DeLuca et al. |
| 6,132,233 A | 10/2000 | Fukuda |

(56) References Cited

U.S. PATENT DOCUMENTS

| | | |
|---|---|---|
| 6,139,350 A | 10/2000 | Mathesius |
| 6,139,360 A | 10/2000 | Hayashi |
| 6,152,778 A | 11/2000 | Dalton |
| 6,155,864 A | 12/2000 | Yoshiura |
| 6,165,017 A | 12/2000 | Kuo |
| 6,168,453 B1 | 1/2001 | Kuo |
| 6,171,139 B1 | 1/2001 | Sato et al. |
| 6,190,385 B1 | 2/2001 | Tom et al. |
| 6,203,354 B1 | 3/2001 | Kuwahara et al. |
| 6,223,088 B1 | 4/2001 | Scharnberg et al. |
| 6,234,827 B1 | 5/2001 | Nishio et al. |
| 6,236,874 B1 | 5/2001 | Devlin et al. |
| 6,246,902 B1 | 6/2001 | Naylor et al. |
| 6,247,963 B1 | 6/2001 | Rattner |
| 6,250,955 B1 | 6/2001 | Archuleta |
| 6,254,425 B1 | 7/2001 | Shchervinsky et al. |
| 6,257,914 B1 | 7/2001 | Comerci et al. |
| 6,257,925 B1 | 7/2001 | Jones |
| 6,280,209 B1 | 8/2001 | Bassler et al. |
| 6,280,227 B1 | 8/2001 | Terada et al. |
| 6,280,243 B1 | 8/2001 | Liu et al. |
| 6,283,789 B1 | 9/2001 | Tsai |
| 6,290,530 B1 | 9/2001 | Chang |
| 6,298,255 B1 | 10/2001 | Cordero et al. |
| 6,324,432 B1 | 11/2001 | Rigaux et al. |
| 6,340,306 B1 | 1/2002 | Daoud |
| 6,356,779 B1 | 3/2002 | Katzenmaier et al. |
| 6,358,083 B1 | 3/2002 | Kraft |
| 6,364,685 B1 | 4/2002 | Manning |
| 6,383,010 B1 | 5/2002 | Mayo et al. |
| 6,383,011 B2 | 5/2002 | Chen |
| 6,383,036 B1 | 5/2002 | Steinhauser et al. |
| 6,386,917 B1 | 5/2002 | Sakaguchi |
| 6,393,317 B1 | 5/2002 | Fukuda et al. |
| 6,394,953 B1 | 5/2002 | Devlin et al. |
| 6,398,575 B1 | 6/2002 | Bresson |
| 6,398,577 B1 | 6/2002 | Simmel et al. |
| 6,411,834 B1 | 6/2002 | Nagai |
| 6,413,112 B2 | 7/2002 | Semmeling et al. |
| 6,415,169 B1 | 7/2002 | Kornrumpf et al. |
| 6,419,636 B1 | 7/2002 | Young et al. |
| 6,434,410 B1 | 8/2002 | Cordero et al. |
| D462,662 S | 9/2002 | Lindekugel |
| 6,447,170 B1 | 9/2002 | Takahashi et al. |
| 6,454,577 B1 | 9/2002 | Yi |
| 6,454,590 B1 | 9/2002 | Goodrich et al. |
| 6,454,605 B1 | 9/2002 | Bassler et al. |
| 6,461,179 B1 | 10/2002 | Sullivan et al. |
| 6,487,430 B1 | 11/2002 | Henderson et al. |
| 6,494,744 B1 | 12/2002 | Lee |
| 6,514,099 B2 | 2/2003 | Endo |
| 6,517,372 B1 | 2/2003 | Jones |
| 6,531,657 B1 | 3/2003 | Jones, Jr. et al. |
| 6,533,600 B1 | 3/2003 | Kashiyama et al. |
| 6,540,549 B2 | 4/2003 | Rupert |
| 6,551,117 B2 | 4/2003 | Poplawski et al. |
| 6,558,189 B2 | 5/2003 | Groebe et al. |
| 6,561,834 B2 | 5/2003 | Chen |
| 6,565,388 B1 | 5/2003 | Van Woensel et al. |
| 6,567,680 B2 | 5/2003 | Swetlik et al. |
| 6,575,759 B1 | 6/2003 | Ollivier |
| 6,575,794 B1 | 6/2003 | Nakamura |
| 6,582,252 B1 | 6/2003 | Lin |
| 6,589,066 B1 | 7/2003 | Wu |
| 6,592,391 B1 | 7/2003 | Wu |
| 6,592,404 B2 | 7/2003 | Endo |
| 6,604,963 B2 | 8/2003 | Lin |
| 6,607,397 B1 | 8/2003 | Zhang et al. |
| 6,609,018 B2 | 8/2003 | Cory et al. |
| 6,609,833 B1 | 8/2003 | Miyachi et al. |
| 6,612,860 B2 | 9/2003 | Droesbeke |
| 6,619,976 B2 | 9/2003 | Huetter et al. |
| 6,619,989 B1 | 9/2003 | Yi |
| 6,636,754 B1 | 10/2003 | Baura et al. |
| 6,648,665 B1 | 11/2003 | Wu |
| 6,648,666 B1 | 11/2003 | Wu |
| 6,654,626 B2 | 11/2003 | Devlin et al. |
| 6,655,979 B1 | 12/2003 | Lee |
| 6,659,790 B1 | 12/2003 | Wu |
| 6,663,412 B2 | 12/2003 | Aramoto et al. |
| 6,663,419 B2 | 12/2003 | Vaden |
| 6,663,420 B1 | 12/2003 | Xiao |
| 6,663,570 B2 | 12/2003 | Mott et al. |
| 6,669,510 B2 | 12/2003 | Yamawaki et al. |
| 6,688,894 B2 | 2/2004 | Knox, Jr. et al. |
| 6,688,907 B2 | 2/2004 | Yamaoka et al. |
| 6,702,602 B2 | 3/2004 | Wu |
| 6,702,603 B2 | 3/2004 | Wu |
| 6,702,616 B1 | 3/2004 | Chang et al. |
| 6,709,284 B1 | 3/2004 | Avlonitis |
| 6,716,165 B1 | 4/2004 | Flanders et al. |
| 6,722,912 B2 | 4/2004 | Wu |
| 6,736,650 B1 | 5/2004 | Chen et al. |
| 6,743,052 B1 | 6/2004 | Lin et al. |
| 6,743,053 B2 | 6/2004 | Wu |
| 6,751,493 B2 | 6/2004 | Wenger |
| 6,755,689 B2 | 6/2004 | Zhang et al. |
| 6,773,293 B1 | 8/2004 | Lee |
| 6,780,065 B2 | 8/2004 | Schwarz |
| 6,786,755 B2 | 9/2004 | Dambach et al. |
| 6,786,764 B2 | 9/2004 | Sivertsen |
| 6,832,928 B2 | 12/2004 | Suzuki |
| 6,837,734 B2 | 1/2005 | Ushio et al. |
| 6,848,926 B2 | 2/2005 | Ling et al. |
| 6,851,969 B2 | 2/2005 | Archuletta |
| 6,860,750 B1 | 3/2005 | Wu |
| 6,866,535 B2 | 3/2005 | Uchida |
| 6,881,098 B2 | 4/2005 | Jeansonne et al. |
| 6,891,379 B2 | 5/2005 | Kelly et al. |
| 6,913,482 B1 | 7/2005 | Wu |
| 6,939,158 B2 | 9/2005 | Moffett et al. |
| 6,939,345 B2 | 9/2005 | KenKnight et al. |
| 6,945,796 B2 | 9/2005 | Bassler et al. |
| 6,945,807 B1 | 9/2005 | Wu |
| 6,948,973 B1 | 9/2005 | Hsu et al. |
| 6,984,143 B2 | 1/2006 | Roese |
| 6,997,733 B2 | 2/2006 | Peng |
| 7,004,787 B2 | 2/2006 | Milan |
| 7,008,255 B1 | 3/2006 | Wang |
| 7,025,618 B2 | 4/2006 | Fukuda |
| 7,025,628 B2 | 4/2006 | LaMeres et al. |
| 7,029,286 B2 | 4/2006 | Hall et al. |
| 7,033,207 B2 | 4/2006 | Nimura |
| 7,041,918 B1 | 5/2006 | Wu |
| 7,056,134 B2 | 6/2006 | Martin et al. |
| 7,056,141 B2 | 6/2006 | Moffett et al. |
| 7,081,008 B2 | 7/2006 | Tan |
| 7,085,598 B2 | 8/2006 | Sato et al. |
| 7,104,801 B1 | 9/2006 | Brodnick et al. |
| 7,110,804 B2 | 9/2006 | Baumer et al. |
| 7,117,590 B2 | 10/2006 | Koenig et al. |
| 7,118,411 B2 | 10/2006 | Huang et al. |
| 7,127,279 B2 | 10/2006 | Finneran et al. |
| 7,128,600 B2 | 10/2006 | Osypka |
| 7,134,908 B2 | 11/2006 | Wu |
| 7,137,839 B2 | 11/2006 | Dilliner et al. |
| 7,144,268 B2 | 12/2006 | Koenig et al. |
| 7,160,136 B2 | 1/2007 | Zhang et al. |
| 7,177,673 B2 | 2/2007 | Matsumura et al. |
| 7,179,111 B2 | 2/2007 | Van Der Mee et al. |
| 7,179,113 B2 | 2/2007 | Koenig et al. |
| 7,182,630 B1 | 2/2007 | Su |
| 7,189,097 B2 | 3/2007 | Benham |
| 7,198,502 B2 | 4/2007 | Koenig et al. |
| 7,201,599 B2 | 4/2007 | Holub |
| 7,207,825 B2 | 4/2007 | LeGallic et al. |
| 7,236,825 B2 | 6/2007 | Wang |
| 7,252,542 B2 | 8/2007 | Chen |
| 7,252,556 B2 | 8/2007 | Anbo et al. |
| 7,252,565 B2 | 8/2007 | Hunter |
| 7,258,566 B2 | 8/2007 | Koenig et al. |
| 7,264,510 B2 | 9/2007 | Koenig et al. |
| 7,270,568 B2 | 9/2007 | Osypka |
| 7,272,427 B2 | 9/2007 | Ristolainen |

(56) References Cited

U.S. PATENT DOCUMENTS

| | | |
|---|---|---|
| 7,275,951 B2 | 10/2007 | Shigeta et al. |
| 7,281,937 B2 | 10/2007 | Reed et al. |
| 7,287,998 B2 | 10/2007 | Masai |
| 7,303,430 B2 | 12/2007 | Butcher |
| 7,318,740 B1 | 1/2008 | Henry et al. |
| 7,322,849 B2 | 1/2008 | Sutton |
| 7,329,139 B2 | 2/2008 | Benham |
| 7,336,985 B2 | 2/2008 | Wallace et al. |
| 7,347,710 B2 | 3/2008 | Ohtaka et al. |
| 7,347,826 B1 | 3/2008 | Karicherla et al. |
| 7,361,058 B1 | 4/2008 | Lien et al. |
| 7,371,102 B2 | 5/2008 | Sakamoto et al. |
| 7,373,196 B2 | 5/2008 | Ryu et al. |
| 7,374,448 B1 | 5/2008 | Jepsen et al. |
| 7,381,082 B2 | 6/2008 | Lai |
| 7,390,224 B2 | 6/2008 | Sodermann et al. |
| 7,396,246 B2 | 7/2008 | Okada et al. |
| 7,399,195 B2 | 7/2008 | Kim et al. |
| 7,401,946 B2 | 7/2008 | Laukhuf |
| 7,402,071 B2 | 7/2008 | Ohtaka et al. |
| 7,413,461 B2 | 8/2008 | Dawiedczyk et al. |
| 7,413,485 B2 | 8/2008 | Lappoehn |
| 7,416,440 B2 | 8/2008 | Homyk et al. |
| 7,422,437 B1 | 9/2008 | Lin et al. |
| 7,422,452 B2 | 9/2008 | Achtner et al. |
| 7,462,074 B1 | 12/2008 | Devlin et al. |
| 7,473,141 B2 | 1/2009 | Liao |
| 7,488,187 B2 | 2/2009 | Wolf |
| 7,494,383 B2 | 2/2009 | Cohen et al. |
| 7,497,731 B2 | 3/2009 | Rosenfeldt et al. |
| 7,497,738 B2 | 3/2009 | Kuo |
| 7,497,740 B2 | 3/2009 | Mei et al. |
| 7,503,807 B2 | 3/2009 | Martin et al. |
| 7,544,089 B2 | 6/2009 | Liu et al. |
| 7,553,184 B2 | 6/2009 | Butcher |
| 7,556,535 B2 | 7/2009 | Liao |
| 7,581,992 B1 | 9/2009 | Liu et al. |
| 7,585,182 B2 | 9/2009 | Asante et al. |
| 7,591,673 B2 | 9/2009 | Chan et al. |
| 7,591,674 B2 | 9/2009 | Sutton et al. |
| 7,604,511 B1 | 10/2009 | Johnson |
| 7,618,262 B2 | 11/2009 | Fogg et al. |
| 7,618,377 B2 | 11/2009 | McAtamney et al. |
| 7,632,130 B2 | 12/2009 | Sami |
| 7,666,028 B2 | 2/2010 | Meleck |
| 7,682,198 B1 | 3/2010 | Plattner |
| RE41,206 E | 4/2010 | Gwiazdowski et al. |
| 7,703,987 B2 | 4/2010 | Kramer et al. |
| 7,713,073 B2 | 5/2010 | Lin |
| 7,717,739 B2 | 5/2010 | Hawkins et al. |
| 7,731,519 B1 | 6/2010 | Swenson, Jr. |
| 7,731,520 B1 | 6/2010 | Daily et al. |
| 7,740,510 B2 | 6/2010 | Muz |
| 7,749,013 B2 | 7/2010 | Sato et al. |
| 7,753,613 B2 | 7/2010 | Tsuji |
| 7,828,583 B2 | 11/2010 | Ohsumi et al. |
| 7,844,316 B1 | 11/2010 | Botero |
| 8,591,427 B2 * | 11/2013 | Zuckerman et al. .......... 600/508 |
| 8,634,901 B2 | 1/2014 | Callahan et al. |
| 2008/0306380 A1 | 12/2008 | Parchk et al. |
| 2009/0099423 A1 | 4/2009 | Al-Ali et al. |
| 2010/0168547 A1 | 7/2010 | Kendricks |

OTHER PUBLICATIONS

PCT International Preliminary Report on Patentability dated Apr. 10, 2014; for PCT Pat. App. No. PCT/US2012/057760; 13 pages.

PCT Search Report dated Mar. 7, 2013; for PCT Pat. App. No. PCT/US2012/057760.

Canadian Office Action dated Aug. 20, 2015; for Canadian Pat. App. No. 2,850,336, 4 pages.

\* cited by examiner

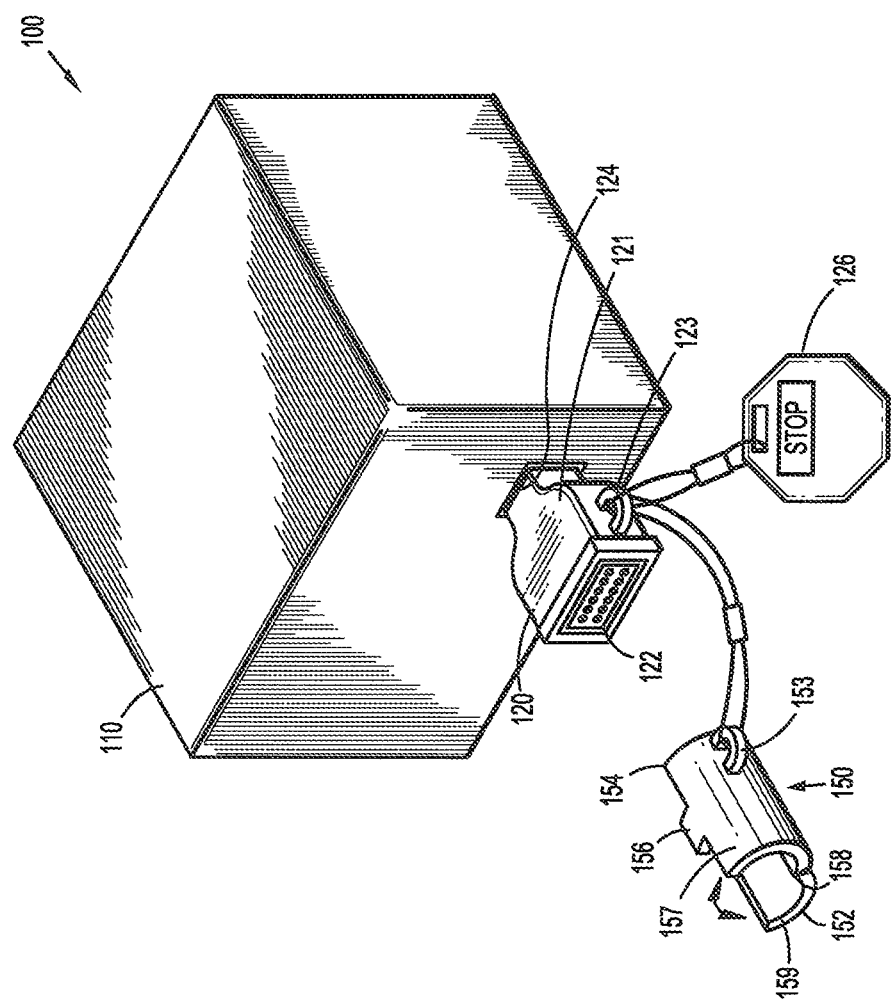

ECG LEADWIRE SYSTEM WITH NOISE SUPPRESSION AND RELATED METHODS

RELATED APPLICATIONS

This is a DIVISIONAL application under 35 U.S.C. §121 of U.S. patent application Ser. No. 13/249,450 (filed Sep. 20, 2011), which is incorporated here by reference in its entirety.

TECHNICAL FIELD

The present disclosure relates to medical equipment. In particular, the present disclosure relates to an electrocardiograph (ECG) leadwire system having improved noise reduction characteristics that includes an ECG lead set, an adapter system, an extension cable, a noise reduction element, and methods for coupling the ECG lead sets with the adapter.

BACKGROUND

ECG lead systems are used to obtain biopotential signals containing information indicative of the electrical activity associated with the heart and pulmonary system. To obtain biopotential signals, ECG electrodes are applied to the skin of a patient in various locations and coupled to an ECG device, e.g., an "ECG monitor" or "ECG telemetry." Placement of the electrodes is dependent on the information sought by the clinician.

The placement of the ECG electrodes on the patient has been established by medical protocols. The most common protocols require the placement of the electrodes in a three-lead, a five-lead, or a twelve-lead configuration. A three-lead configuration requires the placement of three electrodes; one electrode adjacent each clavicle bone (RA, LA) on the upper chest and a third electrode adjacent the patient's lower left abdomen (LL). A five-lead configuration requires the placement of the three electrodes in the three-lead configuration with the addition of a fourth electrode adjacent the sternum (Va) and a fifth electrode on the patient's lower right abdomen (RL). A twelve-lead configuration requires the placement of ten electrodes on the patient's body. Four electrodes, which represent the patient's limbs, include the left arm electrode (LA lead), the right arm electrode (RA lead), the left leg electrode (LL lead), and the right leg electrode (RL lead). Six chest electrodes (V1-V6 leads) are placed on the patient's chest at various locations near the heart. Three standard limb leads are constructed from measurements between the right arm and left arm (Lead I), the right arm and the left leg (Lead II) and the left arm to left leg (Lead III). Other conventional lead configurations include a 14 leads system that incorporated additional leads located on a back surface.

An ECG lead set typically includes an array of three, five, or twelve leads as determined by the intended clinical protocol. Each individual lead wire includes, at a patient end thereof (e.g., distal end), an ECG lead wire connector configured to operably couple the lead wire to an electrode pad affixed to the body of a patient. At the opposite (e.g., proximal) end, the individual lead wires are gathered into a common coupler that is configured to operably couple the array of lead wires to an ECG device. Leads sets are typically provided with a generous length of lead wire sufficient to reach from the patient to the ECG device. In some instances, however, the lead wire may fall short, in which case a lead wire extension cable having appropriate distal and proximal couplers may be employed. In some instances, the lead wire coupler of an ECG lead set and/or ECG lead extension may be incompatible with an available ECG device, in which case an ECG adapter may be employed that facilitates operable coupling of the otherwise-incompatible physical and/or electrical characteristics of the disparate couplers.

Radio frequency interference (RFI), sometime referred to as electromagnetic interference (EMI), is a disturbance that affects an electrical circuit due to either electromagnetic induction or electromagnetic radiation emitted from an external source. The disturbance may interrupt, obstruct, or otherwise degrade or limit the effective performance of a circuit. Biopotential signals are generally very low-level signals, and a typical ECG device has a very high input impedance. As a result, biopotential signals may be susceptible to RFI, particularly from devices that may be in use concurrently in a clinical environment, e.g., an electrosurgical instrument, or a microwave ablation unit. RFI may be exacerbated when an ECG lead wire extension cable is used.

SUMMARY

The present disclosure is directed to a noise-suppressing ECG adapter. In some embodiments the disclosed adapter includes a housing having a first end and a second end, and at least one first connector disposed at the first end of the housing. The at least one first connector is adapted for operably coupling to a proximal end of an ECG lead set. The disclosed adapter includes at least one second connector disposed at the second end of the housing that is adapted for coupling to an input of an ECG device. A noise suppression element is disposed within the housing, and includes one of a ferromagnetic element and an electromagnet having an opening defined therein. A least one conductor operably couples the first connector and the second connector, and passes through the opening defined in the ferromagnetic element. The noise suppression element of the adapter may include a low pass filter, a high pass filter, a notch filter, or a nyquist filter. In some embodiments, a connector includes a six-pin configuration. In some embodiments, the six-pin configuration comprises five signal pins and one ground pin. In some embodiments, a connector includes one signal pin and one ground pin.

In some embodiments, the ferromagnetic element includes a shape selected from the group consisting of a toroid and an open cylinder. The ferromagnetic element may be formed from material selected from the group consisting of ferrite and laminated iron. At least one conductor may pass through the opening of the ferromagnetic element in a plurality of windings.

Also disclosed is a noise-suppressing ECG system. In some embodiments, the disclosed system includes a noise-suppressing ECG adapter, comprising a housing having a first end and a second end, at least one first connector disposed at the first end of the housing, the at least one first connector adapted for operably coupling to proximal end of ECG lead set. The adapter includes at least one second connector disposed at the second end of the housing adapted for coupling to an input of an ECG device. The adapter includes a noise suppression element disposed within the housing, the noise suppression element including a ferromagnetic element having an opening defined therein, and at least one conductor operably coupling the first connector and the second connector and passing through the opening of the ferromagnetic element. The system includes an ECG device adapted to operably couple to the at least one second connector of the noise-suppressing ECG adapter.

In some embodiments, the disclosed noise-suppressing ECG system includes an ECG lead set including a plurality of lead wires at a distal end thereof that are configured to operably couple to a plurality of ECG pads, and at least one ECG connector disposed at a proximal end of ECG leadwire set. The noise-suppressing ECG system, in some embodiments, includes a noise suppression element that includes a low pass filter, a high pass filter, a notch filter and a nyquist filter.

In some embodiments, the disclosed noise-suppressing ECG system includes an ECG adapter having a connector having a six-pin configuration. The six-pin configuration may include five signal pins and one ground pin. Other embodiments may include a connector that contains 12 pins with 2 separate grounds pins. Still other examples may utilize shielded leadwires that use two pins for each contact, one for signal and one for shield.

In some embodiments, the disclosed noise-suppressing ECG system includes an ECG adapter having a connector that includes one signal pin and one ground pin.

In some embodiments, the disclosed noise-suppressing ECG system includes an ECG adapter having a ferromagnetic element that includes a shape selected from the group consisting of a toroid and an open cylinder.

In some embodiments, the disclosed noise-suppressing ECG system includes an ECG adapter wherein the at least one conductor passes through the opening of the ferromagnetic element in a plurality of windings. In another embodiment, electromagnets could be actuated as part of the interface to the ECG monitor so that the magnetic field used to attenuate the electromagnetic interference would only be present when the ECG system was in use.

In some embodiments, the disclosed noise-suppressing ECG system includes an ECG adapter wherein the ferromagnetic element is formed from material selected from the group consisting of ferrite and laminated iron.

Also disclosed is a method of suppressing noise in an ECG system. In some embodiments, the disclosed method includes providing an ECG adapter including an ECG leadwire connector, an ECG device connector, and a noise suppression element. The method includes operably coupling the ECG device connector to an ECG device, and operably coupling an ECG leadwire set to the ECG leadwire connector.

In some embodiments, the disclosed method of suppressing noise in an ECG system includes positioning the noise suppression element around at least a portion of the ECG leadwire set. In some embodiments, the disclosed method of suppressing noise in an ECG system includes a positioning step that further includes closing two semicylindrical halves of a ferromagnetic collar around at least a portion of the ECG leadwire set.

Other advantages, novel features, and objects of the present disclosure will become apparent from the following detailed description of the present disclosure when considered in conjunction with the accompanying drawings, which are schematic and are not intended to be drawn to scale. For purposes of clarity, not every component is labeled in every figure, nor is every component of each embodiment of the present disclosure shown where illustration is not necessary to allow those of ordinary skill in the art to understand the present disclosure.

BRIEF DESCRIPTION OF THE DRAWINGS

Various embodiments of the subject instrument are described herein with reference to the drawings wherein:

FIG. 2A is a schematic view of an embodiment of a noise suppressing collar annexed to an adapter;

DETAILED DESCRIPTION

Figure 1:
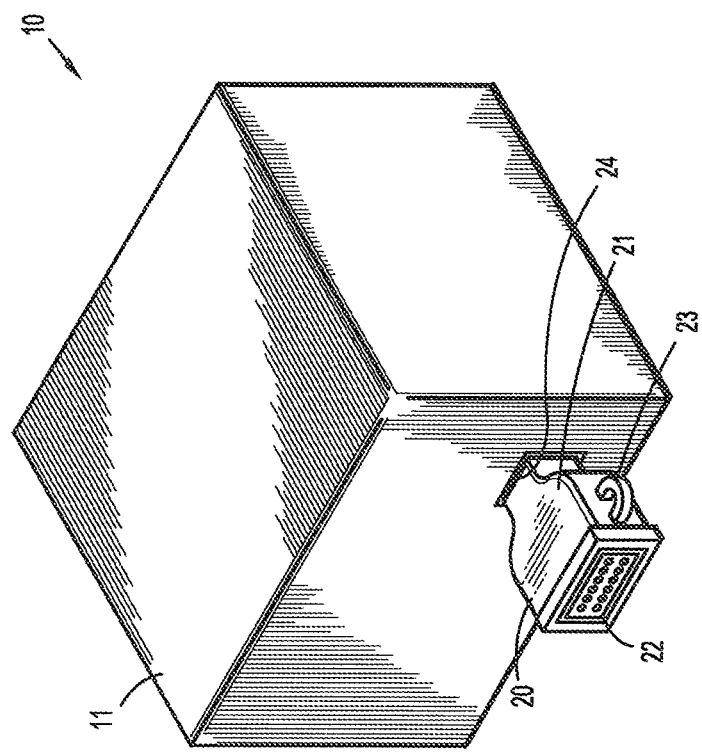
FIG. 1 is a schematic view of an embodiment of a noise suppressing adapter in accordance with the present disclosure.

Particular embodiments of the present disclosure are described hereinbelow with reference to the accompanying drawings; however, it is to be understood that the disclosed embodiments are merely examples of the disclosure, which may be embodied in various forms. The terminology used herein is for the purpose of describing particular embodiments only, and is not intended to be limiting. Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. As used herein, and as is traditional, the term "distal" refers to the portion which is furthest from the user/clinician and the term "proximal" refers to the portion that is closest to the user/clinician. In addition, terms such as "above," "below," "forward," "rearward," etc. refer to the orientation of the figures or the direction of components and are simply used for convenience of description. It is to be understood that embodiments in accordance with the present disclosure may be practiced in any orientation without limitation. In this description, as well as in the drawings, like-referenced numbers represent elements which may perform the same, similar, or equivalent functions. References to connector gender presented herein are for illustrative purposes only, and embodiments are envisioned wherein the various components described can be any of mate, female, hermaphroditic, or sexless gender. Likewise, references to connector types are illustrative in nature, and other connector types, shapes and configurations are contemplated within the scope of the present disclosure.

With reference to FIG. 1, an ECG monitoring system 10 having a noise suppressing ECG adapter 20 is shown. According to one embodiment of the present disclosure, the system 10 enables an end user to use a single ECG leadwire set 30 in association with one or more disparate ECG devices 11, e.g., an ECG monitoring device and/or an ECG telemetry device, as desired. ECG adapter 20 includes an adapter housing 21 having a first end 22 and a second end 24. In the embodiment shown in FIG. 1, first end 22 includes a pin configuration having a six-pin arrangement that is adapted to operably couple with a corresponding, mating six-pin connector 34 disposed at a proximal end of ECG leadwire set 130 having one or more ECG electrode connectors 32 adapted to operatively couple to an ECG electrode pad affixed to a patient. ECG adapter second end 24 includes a pin configuration adapted to mate with a corresponding connector provided by ECG device 11.

Noise suppression element may be formed from any material having suitable electromagnetic, coercivity, and permeability properties, including without limitation, ferrite, laminated iron, and the like. In one embodiment, the noise suppression element is one of a ferromagnetic element and an electromagnet. An electromagnet noise suppression element may draw power from a monitor to which it is connected. An electromagnetic noise suppression element may be actuated as part of an interface to an ECG monitor so that the magnetic field used to attenuate the electromagnetic interference would only be present when the ECG system was in use.

The noise suppression element may include a filter such as a low pas filter, a high pass filter, a notch filter, and a nyquist filter. The passive low pass filter exhibits high impedance at high frequencies typically associated with RFI, which, in turn, attenuates or suppresses RFI within the one or more leadwires 134 and/or high-impedance input circuit of the ECG device.

The pin configurations of first end 22 and/or second end 24 may vary depending on the desired application, the intended ECG device(s) 110 to be used, and the specific lead set or lead sets to be used. For example, and without limitation, pin configuration of first end 22 may include only a single pin used in an unshielded configuration of a single electrode lead set. In another non-limiting example, the pin configuration of second end 24 of ECG connector 20 may include a five-pin male socket connector. In this example, each plug includes a pair of contacts, wherein one plug corresponds to one ECG lead and the corresponding plug corresponds to a ground or shield lead, such as specified by ANSI/AAMI EC53 for shielded leadwire to trunk cable interconnections. The second end 24 of ECG connector 20 may be referred to as monitor plugs. The second end or monitor plugs 24 are configured for coupling to the lead set input connector of ECG device 11.

ECG adapter 20 includes a tether boss 23 that enables one or more tethers, e.g., an additional noise suppressor tether (not shown) and/or a placard tether (not shown), to be affixed thereto. As shown, tether boss 23 includes a u-shaped protuberance having an opening defined therein that extends from an exterior surface of ECG connector 20, however, other tether boss arrangement are contemplated, such as, and without limitation, to a recess with a transverse pin arrangement. A placard annexed to connector 20 may include an inscription conveying operating instructions, e.g., "STOP-Do Not Discard-Reusable" and the like.

Figure 2B:
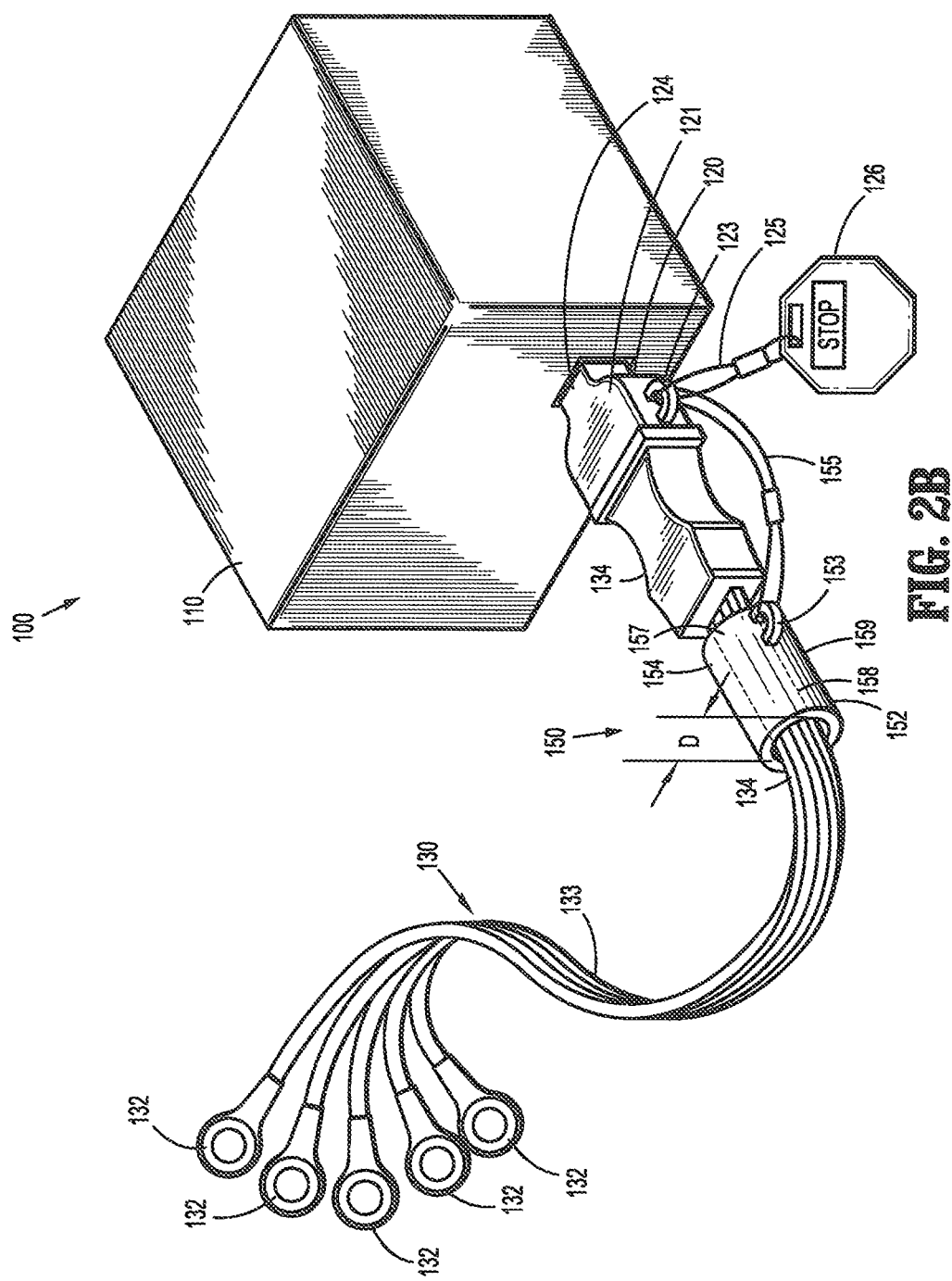
FIG. 2B is a schematic view of an embodiment of the noise suppressing collar of FIG. 2A operatively coupled to a set of leadwires in accordance with the present disclosure.

Turning to FIGS. 2A and 2B, ECG adapter 120 includes a noise suppressor collar 150 that is annexed thereto by noise suppressor tether 155. In one embodiment, adapter 120 does not comprise a noise suppression component within its housing, In one embodiment, the noise suppression element is one of a ferromagnetic element and an electromagnet. An electromagnet noise suppression element may draw power from a monitor to which it is connected. An electromagnetic noise suppression element may be actuated as part of an interface to an ECG monitor so that the magnetic field used to attenuate the electromagnetic interference would only be present when the ECG system was in use.

In another embodiment, adapter 120 may be a noise suppression adapter comprising a noise suppression component within its housing. The noise suppression element in the adapter may, but need not, be of a similar type to that used in the noise suppression collar. For example, the noise suppression element in the adapter may be one of a ferromagnetic element and an electromagnet, while the noise suppression collar may be the other of the ferromagnetic element and the electromagnet. Alternatively, the noise suppression adapter and the noise suppression collar may comprise both a ferromagnetic element or both comprise an electromagnet.

In one embodiment, the noise suppression adapter may comprise a first filter and the noise suppression collar may comprise a second filter, which may, but need not, be the same type of filter as the first filter. For example, the noise suppression adapter may comprise one of a low pass filter, a high pass filter, a notch filter, and a nyquist filter, while the noise suppression collar may comprise a different one of a low pass filter, a high pass filter, a notch filter, and a nyquist filter.

Noise suppressor collar may 150 include a tether boss 153 that is adapted to enable noise suppressor tether 155 to be affixed to collar 150. Noise suppressor collar 150 is selectively configurable between an open configuration as illustrated in FIG. 2A, and a closed configuration as illustrated in FIG. 2B. When configured in a closed configuration, noise suppressor collar 150 has a generally open cylindrical or tubular (e.g., pipe-like or elongate toroid) shape having an inner diameter "D" that is dimensioned to enable one or more ECG leadwires 134 to pass therethrough. In this embodiment, it is believed that noise suppressor collar 150 forms a common mode choke that suppresses RFI induced by stray electromagnetic fields propagating upon the one or more ECG leadwires 134.

Noise suppressor collar 150 may be formed from any material having suitable electromagnetic, coercivity, and permeability properties, including without limitation, ferrite, laminated iron, and the like. The noise suppressor collar may include a filter, such as, a low pass filter, a high pass filter, a notch filter, and a nyquist filter. It is believed that this composition, e.g., ferrite, in cooperation with the open cylindrical or tubular shape of noise suppressor collar 150, forms a passive low-pass filter. The passive low pass filter exhibits high impedance at high frequencies typically associated with RFI, which, in turn, attenuates or suppresses RFI within the one or more leadwires 134 and/or high-impedance input circuit of the ECG device.

In an exemplary embodiment, noise suppressor collar 150 is formed from two generally semi-cylindrical halves consisting of a collar bottom portion 152 and a collar top portion 154 that are joined along a common edge by a hinge 158. In various embodiments, hinge 158 may include a living hinge, a piano hinge, or any suitable hinge arrangement. Collar top portion 154 includes a clasp 156 that is configured to engage a corresponding clasp saddle (not explicitly shown) provided by collar bottom portion 152 to join collar bottom portion 152 and collar top portion 154 in the closed configuration shown in FIG. 2. Noise suppressor collar 150 may additionally or optionally include a jacket 157, 159 covering at least a part of a surface of collar bottom portion 152 and a collar top portion 154. Jacket 157, 159 may be formed from any suitable material, such as a polymeric material including without limitation high density polyethylene, polyurethane, and acrylonitrile butadiene styrene. In an embodiment, jacket 157, 159, and hinge 158 may be integrally formed, e.g., from polypropylene. In this embodiment hinge 158 may be in the form of a living hinge.

During use, a clinician may couple connector 134 of ECG leadwire set 130 with first end 122 of ECG adapter 120. A clinician may separate the two portions 152, 154 of noise suppressor collar 150, e.g., move collar bottom portion 152 and collar top portion 154 to the open configuration as illustrated in FIG. 1. One or more leadwires 134 are positioned between the inner portions of collar bottom portion 152 and collar top portion 154, and the collar bottom portion 152 and collar top portion 154 are moved to the closed configuration as illustrated in FIG. 2. The second end 124 of ECG adapter 120 is mated to an ECG device 110. One or more ECG pads are affixed to a patient, and the one or more ECG electrode connectors 132 are affixed to the one or more ECG pads in accordance with the appropriate protocol (e.g., a three-lead, a five-lead, or a twelve-lead configuration). The ECG device may be activated to commence ECG monitoring, ECG telemetry, and the like.

Figure 3B:
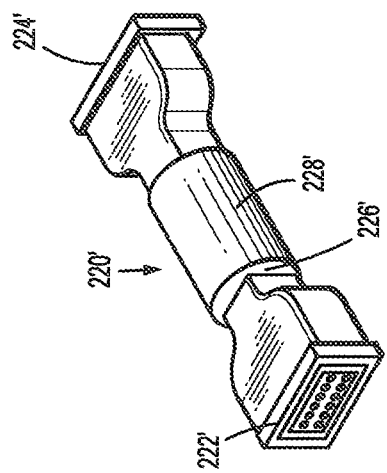
FIG. 3B is a schematic view of a variation of the FIG. 3A embodiment of a noise suppressing collar in accordance with the present disclosure.
Figure 3A:
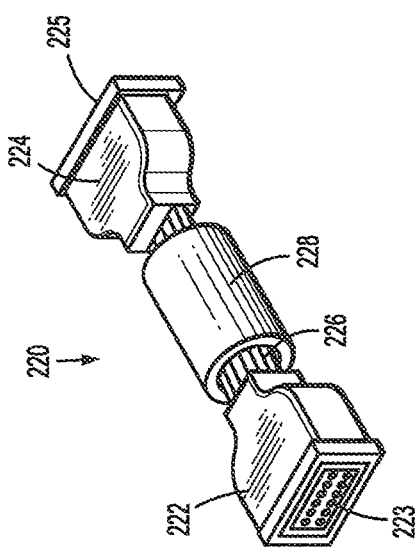
FIG. 3A is a schematic view of another embodiment of a noise suppressing collar in accordance with the present disclosure.
Figure 4:
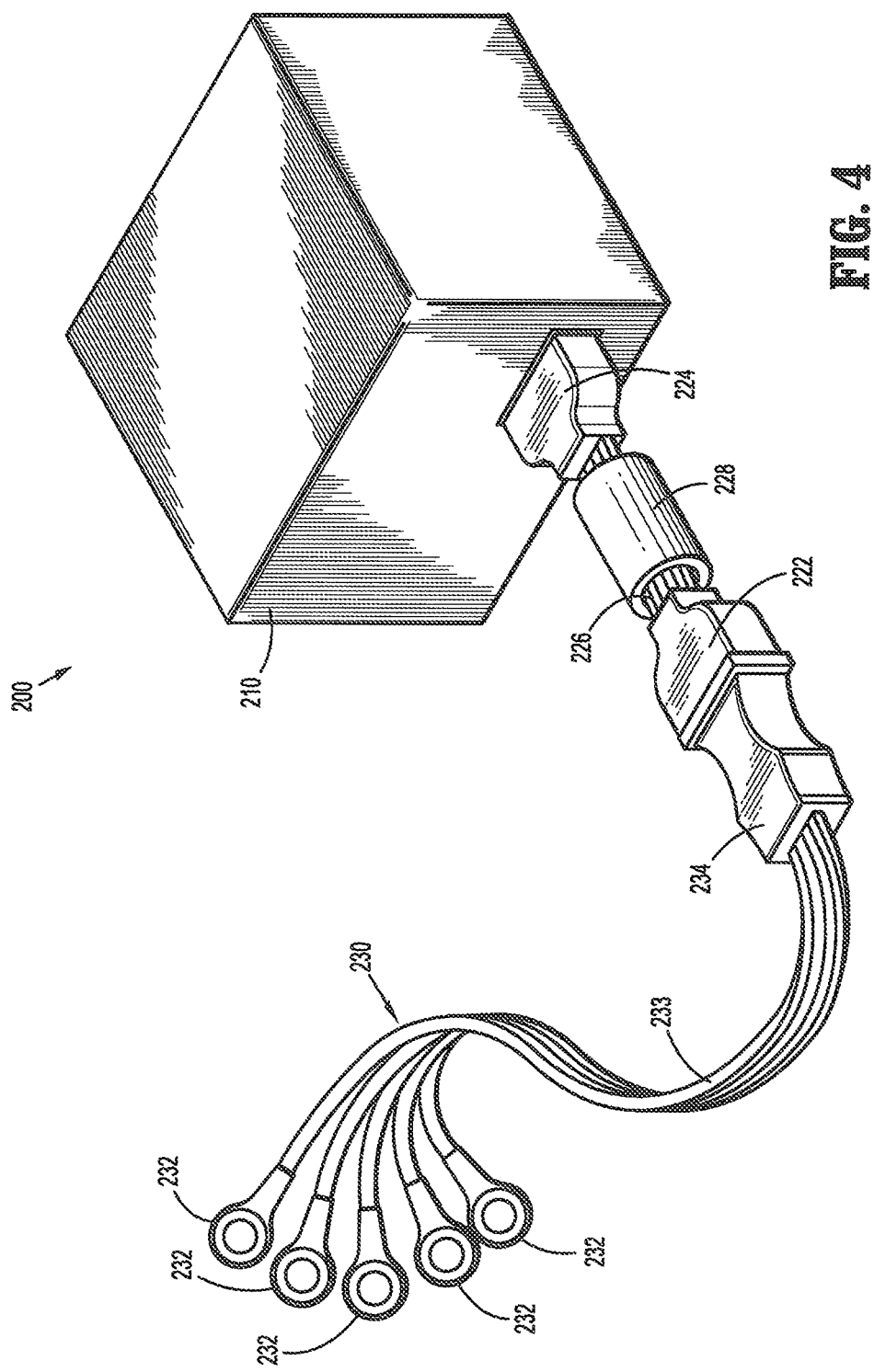
FIG. 4 is a schematic view of the FIG. 3A embodiment of a noise suppressing collar operatively coupled to a set of leadwires in accordance with the present disclosure.

Turning to FIGS. 3A and 4, another embodiment of an ECG adapter 220 in accordance with the present disclosure includes a first end 222 that is operatively coupled to a second end 224 by one or more ECG conductors 226. First end 222 of ECG adapter 220 includes a first connector 223 that is adapted to operably couple with a corresponding, mating six-pin connector 234 disposed at a proximal end of ECG leadwire set 230 having one or more ECG electrode connectors 232 adapted to operably couple to an ECG electrode pad affixed to a patient. ECG adapter 220 second end 224 includes a second connector 225 adapted to mate with a corresponding connector provided by ECG device 210.

ECG adapter 220 includes a noise suppressor collar 228 having a generally open cylindrical or tubular shape (e.g., pipe-like or elongate toroid) that is disposed about at least a portion of the one or more ECG conductors 226. Noise suppressor collar 228 includes an inner diameter that is dimensioned to enable one or more ECG leadwires 226 to pass therethrough. Noise suppressor collar 228 may be formed from any material having suitable electromagnetic, coercivity, and permeability properties as previously described herein, such as, for example, ferrite, laminated iron, and the like. In embodiments, noise suppressor collar 228 may be fixed to the one or more ECG leadwires 226 by any suitable manner of attachment, including without limitation, by an adhesive, by encapsulation, by encasing in heat shrink tubing, and the like. In some embodiments, such as that illustrated in FIG. 3B, an ECG adapter 220' includes a noise suppressor collar 228' that is integrally formed with ECG leadwires 226', a first end 222', and/or a second end 224', wherein ECG adapter 220' is encapsulated in a heat shrink tubing.

During use, as seen in FIG. 4, a clinician may couple connector 234 of ECG leadwire set 230 to first end 222 of ECG adapter 220, and second end 224 of ECG adapter 220 is mated to an ECG device 210. One or more ECG pads are affixed to a patient, and the one or more ECG electrode connectors 232 are affixed to the one or more ECG pads in accordance with the appropriate protocol (e.g., a three-lead, a five-lead, or a twelve-lead configuration). The ECG device may be activated to commence ECG monitoring, ECG telemetry, and the like.

Figure 5A:
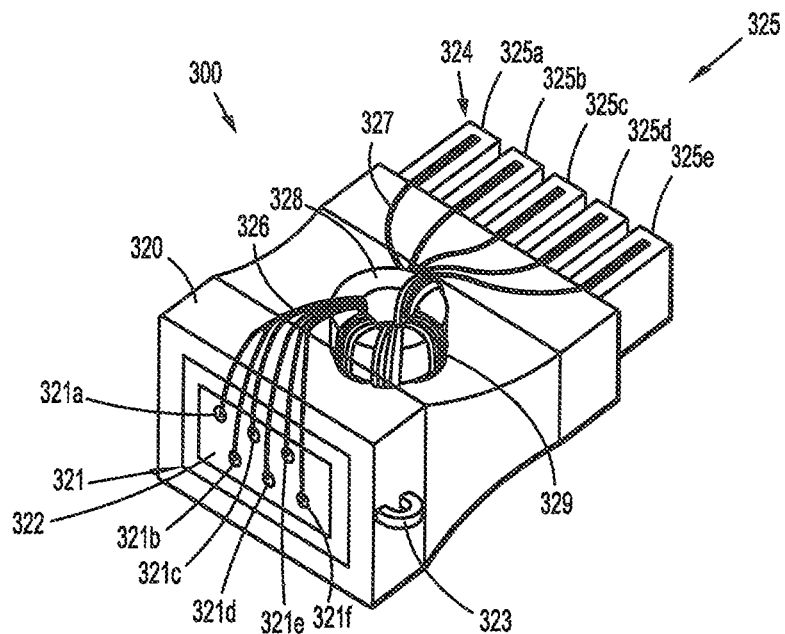
FIG. 5A is a view of still another embodiment of a noise suppressing adapter in accordance with the present disclosure.
Figure 5B:
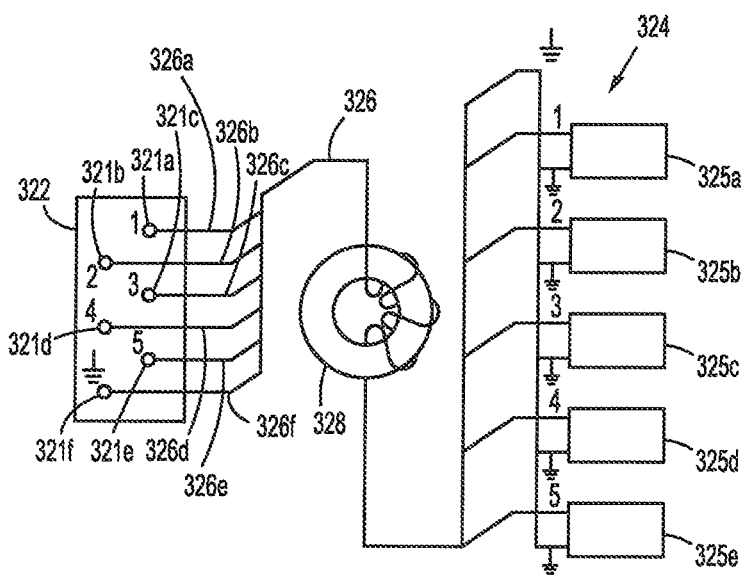
FIG. 5B is a circuit diagram of the FIG. 5A embodiment.

Turning now to FIGS. 5A and 5B, still another embodiment of an ECG noise suppression adapter 300 is presented in accordance with the present disclosure. ECG noise suppression adapter 300 includes a housing 320 having a first end 322 and a second end 324. First end 322 includes one or more input terminals 321a-f that are adapted to operably couple with one or more corresponding, mating pins disposed at a proximal end of ECG leadwire set (not explicitly shown) to receive ECG signals therefrom. Second end 324 of housing 320 of ECG noise suppression adapter 300 includes one or more second connectors 325a-e adapted to mate with one or more corresponding connectors provided by an ECG device. In the present embodiment, the one or more second connectors 325a-e includes a pair of contacts, wherein one plug corresponds to one ECG lead and the corresponding plug corresponds to a ground or shield lead, such as specified by ANSI/AAMI EC53 for shielded leadwire to trunk cable interconnections, as described above.

ECG noise suppression adapter 300 includes a toroidal inductor core 328. Toroidal inductor core 328 may be formed from any material having suitable electromagnetic, coercivity, and permeability properties as previously described herein, such as, without limitation, ferrite and/or laminated iron. One or more ECG conductors 326 are coupled, at a distal end thereof, to one or more input terminals 321a-f. In the present example, six ECG conductors 326 are shown which correspond to input terminals 321a-e (e.g., ECG signals 1 through 5, respectively) and to input terminal 321f that is coupled to a ground (e.g., shield) conductor. The conductors 326 pass around the toroidal inductor core 328 in a plurality of windings to form a low pass choke, or filter, that exhibits high impedance at high frequencies typically associated with RFI as previously described. Conductors 326 may be wound around toroidal inductor core 328 at least one turn, and in some embodiments, may be wound at least five turns, at least ten turns, and/or at least twenty-five turns. In some embodiments, conductors 326 may be grouped and wound collectively, e.g., as a unified cable bundle wound together around toroidal inductor core 328.

In some embodiments, conductors 326 may be individually wound around toroidal inductor core 328. At a proximal end, conductors 326 are operably coupled to corresponding second (output) connectors 325a-e. As shown in FIG. 5B, input pins 321a-e are operably coupled to a signal portion of output connectors 325a-e, respectively, and input pin 321f is operably coupled in common to a ground portion of output connectors 325a-e. It is to be understood that the arrangement and correspondence of inputs and outputs may differ in various and alternative embodiments, particularly where disparate ECG leadwire assemblies are to be coupled to ECG devices that provide differing or non-standard ECG input connectors, as will be appreciated by the skilled artisan.

Housing 320 may be formed from any suitable electrically non-conductive material, including without limitation polymeric material such as polyurethane, polypropylene, polyethylene, acrylonitrile butadiene styrene, polystyrene, polyvinyl chloride, polyacetal, polymethyl methacrylate and acetals. In embodiments, housing 320 may be fabricated by injection molding and/or overmolding around the components of ECG noise suppression adapter 300, e.g., input pins 321a-f and output connectors 325a-e, that mechanically supports and electrically insulates the electrically conductive element(s) therewithin, e.g., toroidal inductor core 328, and/or conductors 326.

Figure 6:
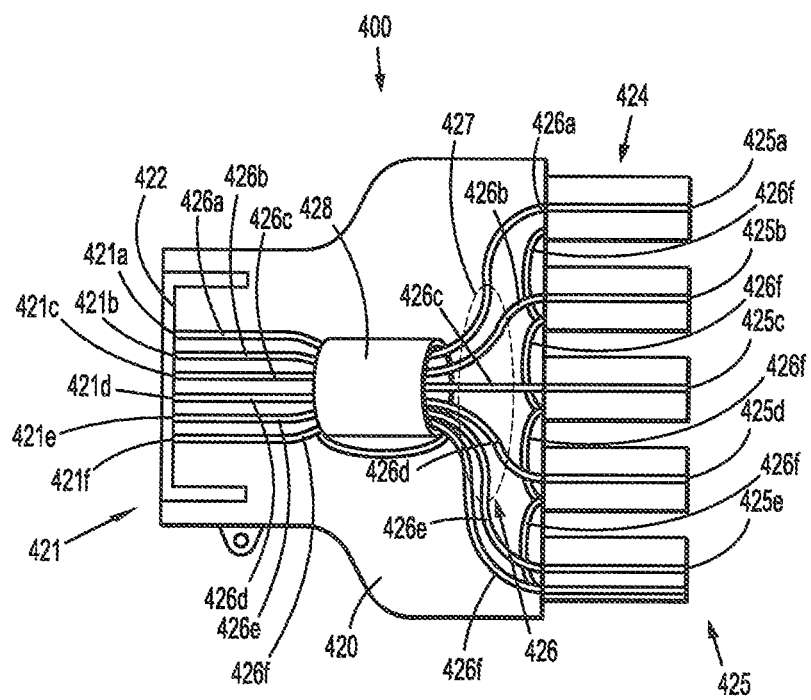
FIG. 6 is a view of yet another embodiment of a noise suppressing adapter in accordance with the present disclosure.

Turning now to FIG. 6, yet another embodiment of an ECG noise suppression adapter 400 is presented. ECG noise suppression adapter 400 includes a housing 420 having a first end 422 and a second end 424. ECG noise suppression adapter 400 includes a noise suppression core 428 that has a generally open cylindrical shape and is formed from any material having suitable electromagnetic, coercivity, and permeability properties as previously described herein, such as, without limitation, ferrite and/or laminated iron. One or more ECG conductors 426 are coupled, at a distal end thereof, to one or more input terminals 421, and at a proximal end thereof, to one or more output connectors 425. In the present example, six ECG conductors 426 are shown wherein input terminals 421a-e corresponding to ECG signals 1 through 5, respectively, are operatively coupled by conductors 426a-e to output connectors 425a-e, respectively. Input terminal 421f is coupled to a ground (e.g., shield) conductor 426f, which, in turn, is coupled to common ground terminals of output connectors 425*a-e*. Conductors 426*a-f* pass through noise suppression core 428 to form a low pass choke, or filter, that exhibits high impedance at high frequencies typically associated with RFI as previously described.

One or more input terminals 421 are adapted to operably couple with one or more corresponding, mating pins disposed at a proximal end of ECG leadwire set (not explicitly shown) to receive ECG signals therefrom. Second end 424 includes one or more second connectors 425 adapted to mate with one or more corresponding connectors provided by an ECG device. At a proximal end, conductors 426*a-f* are operably coupled to corresponding second (output) connectors 425*a-e*. It is to be understood that the arrangement and correspondence of inputs and outputs may differ in various and alternative embodiments, particularly where disparate ECG leadwire assemblies are to be coupled to ECG devices that provide differing or non-standard ECG input connectors, as will be appreciated by the skilled artisan.

Housing 420 may be formed from any suitable electrically non-conductive material, including without limitation polymeric material such as polyurethane, polypropylene, polyethylene, or acrylonitrile butadiene styrene. In embodiments, housing 420 may be fabricated by injection molding and/or overmolding around the components of ECG noise suppression adapter 400, e.g., input pins 421*a-f* and output connectors 425*a-e*, to mechanically support and electrically insulate the electrically conductive element(s) therewithin, e.g., noise suppression core 428, and/or conductors 426.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A noise-suppressing ECG adapter, comprising:
a housing having a first end and a second end;
at least one first connector disposed at the first end of the housing, the at least one first connector adapted for operably coupling to a proximal end of an ECG lead set;
at least one second connector disposed at the second end of the housing, the at least one second connector adapted for coupling to an input of an ECG device;
a noise suppression element disposed within the housing, the noise suppression element including one of a ferromagnetic element and an electromagnet having an opening defined therein; and
at least one conductor operably coupling the first connector and the second connector and passing through the opening of the one of the ferromagnetic element and the electromagnet,
wherein the noise suppression element includes the ferromagnetic element formed from material selected from the group consisting of ferrite and laminated iron.

2. The noise-suppressing ECG adapter according to claim 1, wherein the noise suppression element includes one of a low pass filter, a high pass filter, a notch filter, or a nyquist filter.

3. The noise-suppressing ECG adapter according to claim 1, wherein the at least one first connector includes a six-pin configuration.

4. The noise-suppressing ECG adapter according to claim 3, wherein the six-pin configuration comprises five signal pins and one ground pin.

5. The noise-suppressing ECG adapter according to claim 1, wherein the at least one second connector includes one signal pin and one ground pin.

6. The noise-suppressing ECG adapter according to claim 1, wherein the one of the ferromagnetic element and the electromagnet includes a shape selected from the group consisting of a toroid and an open cylinder.

7. The noise-suppressing ECG adapter according to claim 1, wherein the at least one conductor passes through the opening of the ferromagnetic element in a plurality of windings.

8. A noise-suppressing ECG system, comprising:
a noise-suppressing ECG adapter, comprising:
a housing having a first end and a second end;
at least one first connector disposed at the first end of the housing, the at least one first connector adapted for operably coupling to proximal end of an ECG lead set;
at least one second connector disposed at the second end of the housing, the at least one second connector adapted for coupling to an input of an ECG device;
a noise suppression element disposed within the housing, the noise suppression element including one of a ferromagnetic element and an electromagnet having an opening defined therein; and
at least one conductor operably coupling the first connector and the second connector and passing through the opening of the one of the ferromagnetic element and the electromagnet; and
an ECG device adapted to operably couple to the at least one second connector of the noise-suppressing ECG adapter,
wherein the noise suppression element includes the ferromagnetic element formed from material selected from the group consisting of ferrite and laminated iron.

9. The noise-suppressing ECG system according to claim 8, further comprising the ECG lead set including a plurality of lead wires at a distal end of the ECG lead set configured to operably couple to a plurality of ECG pads, and an ECG connector disposed at a proximal end of the ECG lead set.

10. The noise-suppressing ECG system according to claim 8, wherein the noise suppression element includes one of a low pass filter, a high pass filter, a notch filter and a nyquist filter.

11. The noise-suppressing ECG system according to claim 8, wherein the at least one first connector includes a six-pin configuration.

12. The noise-suppressing ECG system according to claim 11 wherein the six-pin configuration comprises five signal pins and one ground pin.

13. The noise-suppressing ECG system according to claim 8, wherein the at least one second connector includes one signal pin and one ground pin.

14. The noise-suppressing ECG system according to claim 8, wherein the one of the ferromagnetic element and the electromagnet includes a shape selected from the group consisting of a toroid and an open cylinder.

15. The noise-suppressing ECG system according to claim 14, wherein the at least one conductor passes through the opening of the ferromagnetic element in a plurality of windings.

16. A removable radio frequency interference (RFI) noise-suppressing ECG adapter, comprising:

a housing having a first end and a second end;
at least one first connector disposed at the first end of the housing, the at least one first connector adapted for operably coupling to a connector of an ECG lead set that is adapted to connect to an ECG monitoring device;
at least one second connector disposed at the second end of the housing, the at least one second connector adapted for coupling to an external input connector of the ECG monitoring device that is adapted to connect to the connector of the ECG lead set;
an RFI noise suppression element disposed within the housing, the noise suppression element including one of a ferromagnetic element and an electromagnet having an opening defined therein; and
at least one conductor operably coupling at least one pin of the first connector and at least one pin of the second connector and passing through the opening of the one of the ferromagnetic element and the electromagnet;
wherein the ECG adapter is a removable adapter configured to be installed external to the ECG monitoring device and between the ECG monitoring device and the ECG lead set to suppress RFI noise,
wherein the RFI noise suppression element includes the ferromagnetic element formed from material selected from the group consisting of ferrite and laminated iron.

* * * * *